United States Patent [19]

Barer

[11] 4,226,881

[45] Oct. 7, 1980

[54] INSECTICIDAL COMPOSITIONS

[75] Inventor: Sol J. Barer, Clark, N.J.

[73] Assignee: Celanese Corporation, New York, N.Y.

[21] Appl. No.: 779,167

[22] Filed: Mar. 18, 1977

Related U.S. Application Data

[63] Continuation of Ser. No. 631,962, Nov. 14, 1975, abandoned.

[51] Int. Cl.³ .................... A01N 31/00; A01N 43/08; A01N 47/10
[52] U.S. Cl. .............................. 424/285; 424/273 P; 424/275; 424/300; 424/343
[58] Field of Search .................. 424/285, 300, 343

[56] References Cited

U.S. PATENT DOCUMENTS

| | | | |
|---|---|---|---|
| 3,203,853 | 8/1965 | Jager et al. | 424/300 |
| 3,336,186 | 8/1967 | Peissker et al. | 424/300 |
| 3,553,328 | 1/1971 | Koundakjian | 424/343 |
| 3,755,374 | 8/1973 | Zumach et al. | 424/285 |

OTHER PUBLICATIONS

Chemical Abstracts, vol. 82 (1975), p. 12080g.

*Primary Examiner*—Leonard Schenkman
*Attorney, Agent, or Firm*—Kenneth A. Genoni

[57] ABSTRACT

Enhancement of biological effectiveness of carbamate insecticide compositions with alkanediols.

6 Claims, No Drawings

INSECTICIDAL COMPOSITIONS

This application is a continuation of U.S. Ser. No. 631,962 filed Nov. 14, 1975, now abandoned.

This invention is concerned with the enhancement of the biological activity of insecticides, and in particular the carbamate insecticides, with alkanediols.

The carbamate insecticides constitute a well-known class of insecticides which are becoming of increased commercial importance, particularly as replacements for the organochlorine insecticides the latter being carefully regulated in recent time because of their possible adverse effect on human health. The carbamate insecticides are employed in the control of a broad spectrum of insects including aphids, mites, wire worms, corn rootworm, alfalfa weevil, sugarcane borers, rice water weevil, cabbage looper, southern armyworm, tobacco budworm, corn earworm and houseflies. In general, the carbamate insecticides are useful in the control of insects on various agricultural plants including cotton, rice, sugarcane, vegetable and fruit as well as ornamental plants. The toxicity of the carbamates in this activity is attributable to cholinesterase and acetylcholinesterase inhibition in the insects affected.

As with most insecticides in general, new research effort is directed to reducing the amount of carbamate insecticide needed for insect control, both from the viewpoint of the obvious economics to be realised by the use of less insecticide and from the ecology viewpoint since the insecticides can have harmful effects on pollinating insects which, of course, are most beneficial. Thus, the direction of the research effort is to reduce the amount of insecticide needed per application, and/or to increase the effectiveness of each application of the insecticide to the infested substrate, i.e. to enhance the insecticides in their biological activity.

The enhancement of insecticides in their biological activity relates to apparently increasing the toxic effect thereof. Generally, enhancement therefor occurs where a higher mortality rate is obtained in the presence of the potentiating agent as contrasted with the use of the insecticide alone. Instances of enhancement of insecticides have been reported in the literature. For example (Chem. Abst. 45,6340 and 7149) potentiation of certain ovicides and miticides i.e., dodecyl thiocyanate, azobenzene and azoxybenzene, is attributed to benzyl alcohol, as well as p-tolylcarbinol, piperonyl alcohol, phenylethanol, phenylpropanol, benzyl cresol and 2,4-xylen-1-ol. Enhancement of the miticidal activity of propargyl 2-(p-tert.-butylphenoxy) cyclohexyl sulfite by certain mixed polyoxyalkylene ether copolymers is described in U.S. Pat. No. 3,839,554. Similarly, enhanced mite ovicidal activity of 2-aminobenzimidazole carboxylic acid esters by surfactants is described in U.S. Pat. No. 3,427,388.

Aliphatic glycols have been suggested for pesticidal compositions as a component of a liquid spray adjuvant for use in the spray application of the compositions of the aforesaid U.S. Pat. No. 3,839,554; as humectants for mite ovicidal compositions described in the aforesaid U.S. Pat. No. 3,427,388; as a dispersant to ensure proper fine droplet size of agricultural sprays as described in U.S. Pat. No. 3,764,293; for their freeze resistance in agricultural concentrate compositions stabilized with methyl cellulose as described in U.S. Pat. No. 3,399,991; as a solvent (propylene glycol) for naphtho-quinone carbamate spray compositions in U.S. Pat. No. 3,705,914; and as a carrying agent for agricultural concentrates which are non-corrosive to metal as described in U.S. Pat. No. 2,510,839. U.S. Pat. No. 2,606,876 suggests the use of glycols among other alcohol solvents, as solvent system for a stabilizer composition to be added to a herbicidal concentrate composition.

The carbamate insecticides are characterised by the presence of the carbamate functional group,

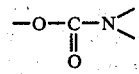

and the mono- and dithio analogs thereof, wherein the residual valences on the terminal oxygen (or sulfur) and nitrogen, respectively, are occupied by hydrocarbon and/or heterocyclic radicals with such radicals optionally including various substituents such as amino, hydroxy, halo, nitro, and the like. Numberous carbamate insecticides are described in the patent literature including the following U.S. Pat. Nos. 3,474,170; 3,474,171; 3,564,605; 3,655,696; 3,547,955; and 3,755,374 (which describe benzofuranyl and dihydrobenzofuranyl carbamates); 3,548,058 (chromanyl carbamates); 3,592,897 (benzylthiolcarbamates); 2,951,786 (pentahalophenyl N-phenyl carbamates); 3,408,323 (naphthyl carbamates); 3,301,748 (aryldithio carbamates); 2,903,478 and 3,203,853 (arylcarbamates).

Many carbamate insecticides are now commercially employed including products under the generic names, carbofuran (Furadan-FMC Corp.); carbaryl (Sevin-Union Carbide); methomyl; aldicarb (Temik-Union Carbide); propoxur (Baygon-Mobay Chemical); and bufencarb (Bux, Ortho Chemical).

THE INVENTION

It has now been discovered that enhancement of carbamate insecticides can be realized by the use of alkanediols which improve the biological activity of the insecticides to obtain a greater contact mortality rate than obtainable with the insecticide alone.

As is well-known, insecticides function in two ways: by direct contact with the insect, i.e. contact efficacy, and by the indirect route of being absorbed by the substrate, all or part of which is consumed by the insect, i.e. the systemic route, or the so-called "stomach poison" route. In the indirect route, the substrates, e.g. plants, are treated with the insecticidal composition which is absorbed systemically and is usually found in the plant fluids. The insects then imbibe the plant juices containing the insecticide and the toxic effect thereof is thus realized.

In the present experience, the enhancement of the biological activity of the present miticides by alkanediols occurs only with respect to the direct contact route, there being little, if any, enhancement of the systemic route. Thus, when foliar sprays of the present compositions are applied to plants before infestation by the selected insects, little or no enhancement occurs, and in some cases there is evidence of inhibitory action by the alkanediols in that the insecticide is more active in the absence of the alkanediol, i.e. the control containing no alkanediol shows greater activity by the systemic route.

This is indeed surprising in view of the prior art in which no such distinction either appears or is recognized with respect to enhancement of the biological activity of insecticides, especially the carbamate insecticides. In general, reference to enhancement of biological activity of insecticides, and in particular miticides, embraces not only the contact activity but also the systemic activity (see for example U.S. Pat. Nos. 3,427,388 and 3,839,554).

As is customary, the insecticide is provided in a form which lends itself to liquid application usually with aqueous vehicles and may, in fact, be provided in aqueous form, conveniently concentrated, which is diluted with water for actual use. Alternatively, the insecticide can be provided in dry form suitable for reconstitution with a vehicle, e.g. water. The insecticide can also be dissolved where soluble, or suspended in the selected alkanediol, with or without diluent. The enhancing agents of this invention can be provided in the concentrated form of the insecticidal preparation, or, along with vehicle used as diluent.

To determine the efficacy of the selected diol, it is formulated with the insecticide and tested on various insect species at varying levels of diol in the formulation employed. Thereafter, a comparison of the results obtained with and without the diol will indicate higher biological activity for those formulations where enhancement occurs. Of course, where the results obtained show no distinction, no enhancement is realized. Such determination amounts to routine experimentation based on screening techniques which are employed in testing laboratories almost on a daily basis. With the teachings of the present invention, i.e. that alkanediols do enhance insecticides in their specific activity, the determination of specifics with regard to insecticide, substrates, optimum levels of potentiating agent and the like are readily carried out using standard test procedures.

Suffice is to say that the present invention is predicated on the discovery that alkanediols to enhance the biological activity of carbamate insecticides against a variety of insects and the invention embraces only insecticidal compositions of enhanced activity wherein the enhanced activity is due to the presence of an alkanediol, as defined hereinafter.

DESCRIPTION OF THE INVENTION

The alkanediols to be employed in the present new compositions preferably contain up to about 6 carbon atoms and comprise ethanediol; 1,2-propanediol; 1,3-propanediol; 1,3-butanediol; 1,4-butanediol, 1,6-hexanediol; and isomers of the higher carbon content diols, e.g. 2-methyl-2, 4-pentanediol. Of the preferred diols, the most preferred are the butanediols, i.e. 1,3 and 1,4-butanediol, since best results are obtained therewith.

Preferred carbamates are represented by the formula

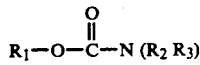

in which $R_1$ is an aryl, substituted aryl, heterocyclic, or substituted heterocyclic radical, preferably containing up to 10 ring-carbon atoms; $R_2$ is hydrogen or lower alkyl and $R_3$ is lower alkyl. Representative aryl groups include phenyl and naphthyl which may be substituted with one, or more substituents such as lower alkyl, lower alkoxy, hydroxy, amino, lower alkyl (mono- and di-) substituted amino, halo and lower alkylthio groups. Such substituents also include carbamyl and alkyl-substituted carbamyl. Heterocyclic radicals include nitrogen, oxygen and sulfur heterocyclic radicals such as thiophene, furan, pyrolle, oxazole, pyrazine, pyridine, thiazole, benzofuran, benzothiophene, and benzoxazole radicals, and fully or partially hydrogenated derivatives such as 2,3-dihydrobenzofuran, piperidine, and the like. The heterocyclic radicals may be substituted with one or more of the aforesaid substituents. Examplary carbamates include compounds such as
1-napthyl N-methyl carbamate,
(2,3-dihydro-2, 2-dimethyl-7-benzofuranyl),
N-methyl carbamate,
m-[N-(dimethylaminomethylene) amino] phenyl N-methyl carbamate,
2-isopropylphenyl N-methyl carbamate,
2-isopropoxyphenyl N-methyl carbamate,
3-(1-methylbutyl) phenyl N-methyl carbamate,
3-(1-ethylpropyl) phenyl N-methyl carbamate,
6-chloro-3,4-xylenyl N-methyl carbamate,
4-methylthio-3,5-xylenyl N-methyl carbamate,
1-naphthyl N-ethyl carbamate,
1-naphthyl N-isopropyl carbamate,
1-naphthyl N-butyl carbamate,
1-naphthyl N-hexyl carbamate,
1-(4-chloronaphthyl) N-methyl carbamate,
1-(5,6-dihydronaphthyl) N-methyl carbamate,
1-(5,8-dihydronaphthyl) N-methyl carbamate,
4-benzothienyl N-methyl carbamate,
1-phenyl-3-methylpyrazol-5-yl N,N-dimethyl carbamate,
2-(N,N-dimethyl carbamyl)-3-methylpyrazol-5-yl N,N-dimethyl carbamate,
and mixtures thereof.

The methods of preparing such compounds are fully described in the literature e.g. U.S. Pat. Nos. 2,903,478; 3,203,853, as well as the method of using the carbamates as insecticides.

Preferably, the carbamate compounds are employed at effective levels of the order of magnitude of parts per million, whereas for flying insects e.g. houseflies, the concentration of insecticide will be about ten to twenty thousand parts per million. As with any insecticide composition, the amount of active ingredient employed is that which is required to attain effective insecticidal activity and excessive amounts are usually avoided for reasons of economy and ecology.

The amount of potentiating agent will also vary within wide limits, but, as with the insecticide, no practical advantage is realized by use of excessive amounts which probably will accomplish little but will increase the cost of the formulation. In general, the operable range of potentiating agent is from as little as about 1% by weight to as much as about 50% by weight based on the total spraying composition, although for most applications from about 2 to about 10% by weight is preferred. When greater than 10 percent of diols is employed, phytotoxic effects on the treated plants may occur. In addition, with higher concentration of potentiating agent, the formulations may tend to lose homogeneity and separate into phases which however can be overcome by frequent agitation of the composition during application. Thus, at levels of 20% and higher, e.g. 50%, the separation of phases may occur and the formulation would be considered poor for that reason, although operable for the intended use. In the results obtained to the present, the potentiating agents of the invention have shown remarkable increases in the toxicity of the carbamate insecticides in the preferred range of diol tested.

In determining efficacy of the present new compositions, it was found that levels of potentiating agent in excess of about 10 volume-percent usually result in phytotoxicity, resulting in damage to plants. For agricultural application, i.e. direct spraying of plants, it is preferably to use less than 10% of the potentiating agent, and to even further minimize such undesirable effects, concentration of 5% by weight or less is even more preferred.

For the purpose of determining the insecticides which are enhanced in their biological activity, a simple test procedure can be employed prior to actual biological testing whether in vivo or in vitro.

In present experience, the insecticides for which significant enhancement is noted are usually soluble in the diol employed. Generally, insecticides which are not soluble are not enhanced as to their insecticidal activity, but most which are soluble will shown enhanced activity when biologically tested. Thus, by the use of simple solubility determination, it is possible to determine bioactive agents which are enhanced in accordance with the present invention. Generally, the insecticide should be soluble to the extent of at least 50% by weight in the diol.

The exact mechanism by which the present agents enhance the biological activity of insecticides is not fully understood. The data obtained in testing compositions in accordance with the invention appear to suggest potentiation of the insecticide as contrasted with synergistic effects. In the main, insecticidal synergists function by preventing the detoxification of the insecticide and are usually somewhat complex compounds. However, analysis of data obtained with the present new compositions suggests possible synergism, especially at low levels of the insecticide and the enhancing agent where unexpectedly high mortality of the tested insects is noted.

Usually, potentiating agents have little, if any, insecticidal properties. However, the diols of this invention, especially 1,3-butanediol have surprisingly shown biocidal activity which is at least moderately significant. For example, 1,3-butanediol alone, showed 43% aphid control. In 2% aqueous mixture, 1,3-butanediol controls 37% of Bacterial Leaf Spot (tomato) and 25% of Leaf Rust of Wheat, with no injury to either plant species. 5% aqueous 1,3-butanediol gave 27% contact mortality on mites, but little efficacy as a foliar spray on plants for control of mites by the systemic route.

In summary, the results suggest potentiation which results in enhanced activity of the insecticide, but synergistic effects can be explanatory of at least part of the mechanism, particularly where low concentrations of insecticide are employed. Regardless of the mechanism by which the present new compositions are of enhanced biological activity, the present invention provides greater mortality rates than attainable by the insecticide when used alone and provides a significant advance in the control of insects.

The present enhancing agents include compounds which are readily available in commercial quantities at relatively low cost, especially the presently preferred 1,3-butanediol, which also has FDA approval in many areas of use, e.g. as a humectant in cellophane and in tobacco. For these reasons, coupled with the results obtained in enhancing insecticidal action, the said compound is preferred.

As with any insecticidal compositions, the present new compositions may also contain other biologically active materials, including other agricultural agents, e.g. bactericides, fungicides, nematocides, insecticides, fertilizer, fruit-thinning agents, and the like; surfactants and other additives such as corrosion inhibitors and anti-foaming agents commonly employed in such compositions. The surfactants used are surface-active agents which are acceptable for agricultural use. These are well-known in the art and are described in the patent literature, e.g. see U.S. Pat. No. 3,427,388.

As mentioned hereinbefore, it is preferred to provide concentrates of the compositions of this invention for eventual use in spraying applications. The concentrates are prepared at concentrations of the active ingredients to provide the required levels of insecticide and alkanediol for the intended purpose, i.e. as a spray for application to the infested substrate. Commonly, the concentrates are diluted with water and spray-applied using standard techniques and equipment.

The concentrates are preferably comprised of solutions of the insecticide in the selected alkanediol which may range in concentration from as little as about 0.05% to the saturation concentration of the insecticide in the selected diol. Where the insecticide is of limited solubility, e.g. less than 1% or 2% by weight, any excess over the solubility can be provided by merely suspending the insecticide in the alkanediol. In the latter instance, in particular, and preferably in all concentrates, a surfactant or dispersing agent may be incorporated into the concentrate to maximize uniform dispersion of the insecticide in water when the concentrate is used for spray applications. Most commonly, the amount of insecticide in the concentrate will range from about 0.05 to as much as about 10% by weight based on the weight of alkanediol, and preferably from about 2 to about 5% by weight. The concentrates may contain water or other diluents such as alcohols, e.g. isopropanol, or hydrocarbon solvents, e.g. petroleum ethers, and the like. Large quantities of water are avoided since the presence of water is not required and water can be added to the concentrate as needed when used in spray application, but small quantities of water, e.g., 1–2% by volume, can be present. Solvent diluents can be present in amount ranging up to about 50% by volume. The use of solvent diluents in the concentrate can be for the purpose of replacing the alkanediol with a less expensive solvent, or to increase the solubility of the miticide in the concentrate liquid system. The concentrates are diluted with water to provide the spray concentrations required in actual application. The dilution can be accomplished by aspiration of the concentrate into a stream of spray of water using known aspirator-type spray apparatus, or alternatively by direct dilution with water to specified concentrations after which the diluted concentrate is then spray-applied using known pressure-spray applicators. Accordingly, a concentrate comprising 0.05% by weight insecticide in an alkanediol on dilution with water at a ratio of 20:1 provides a spray composition in which the diol is at 5% by weight and the insecticide at 25 ppm, while a 1% solution on the same dilution would provide a spray composition in which the diol is at 5% by weight and the insecticide at 500 ppm. Thus, by selecting suitable concentrates of known concentrations, a spray composition of any desired concentration of insecticide and diol can be produced.

In a preferred embodiment of the invention, the alkanediol is employed in a composition in which the amount of insecticide present is less than that which provides maximum toxicity. Thus, whereas a low mortality is normally realized with a given level of carbamate insecticide, the mortality rate is significantly increased by the presence of an alkanediol. For example, at 25 ppm of (2,3-dihydro-2, 2-dimethyl-7-benzofuranyl) N-methyl carbamate, the mortality rate for 2-spotted mites is less than 5% but when an alkanediol is added at 2.5% by weight of the spraying composition the mortality rate increases as much as 10-12 times. With 1-naphthyl N-methyl carbamate, the housefly mortality at 2500 ppm was increased from 23% to almost 60% by inclusion of 1,3-butanediol at 10% of the spray composition. Accordingly, such compositions in which lower than normal levels of insecticide are employed along with an alkanediol are more desirable from both the economic and ecological viewpoints. In general, the significant aspects of this preferred form of the invention are realized when employing the insecticide at a level of effectiveness of less than about 50%.

The following examples are given to further illustrate the invention.

EXAMPLE I

Contact miticidal effectiveness of (2,3-dihydro-2, 2-dimethyl-7-benzofuranyl) N-methyl carbamate (hereinafter referred to as Furadan for convenience.)

The test procedure employed is as follows:

Individually potted horticultural beans at growth stage when the primary leaves are approximately one inch long are infested with two-spotted spider mites (*Tetranychus urtical*) 24 hours prior to treatment, ensuring establishment of adults and egg deposition at the time of treatment. Upper and lower surfaces of infested host plants are alternately sprayed at 20 psi to incipient run off, allowed to air dry under laboratory conditions and then removed to greenhouse holding racks provided with subterranean water source. Three test plants are used for each test unit.

Miticidal and phytocidal observations are made 72 hours after treatment by removing one leaf from each test plant. Phytotoxicity is rated on a zero (no injury) to ten (death of the test plant) scale.

Spray compositions of Furadan in 1,3-butanediol at the indicated concentrations are prepared and tested as to miticidal activity with the results indicated in Table I.

TABLE I
Potentiation of Miticidal Activity of Furadan

| Con. Furadan (ppm) | Con. 1,3-butanediol | % Mortality (72 hrs.) |
|---|---|---|
| 50 | 0 | 81 |
| 50 | 1% | 97 |
| 50 | 2.5% | 98 |
| 50 | 5.0% | 95 |
| 25 | 0 | 36 |
| 25 | 1% | 81 |
| 25 | 2.5% | 95 |
| 25 | 5.0% | 93 |
| 12.5 | 0 | 14 |
| 12.5 | 1% | 24 |
| 12.5 | 2.5% | 50 |
| 12.5 | 5% | 68 |

EXAMPLE 2

The procedure of Example 1 is repeated using 1,3-propanediol, ethylene glycol, 1,3-butanediol and 1,4-butanediol at levels of 2.5% diol and 25 ppm of Furadan. The results are given in Table II. In these tests, the miticide is mixed with the diol and then diluted to the desired concentration with de-ionized water containing 0.05% Tween 20 (polyoxyethylene ethers of mixed partial oleic acid esters of sorbitol anhydride).

TABLE II

| Treatment Applied | Concentration ppm | percent | Ave % Mortality (48 hours): Plant injury (0–10 scale) Run 1 | Run 2 |
|---|---|---|---|---|
| Furadan | 25 | | 4:0 | 2:0 |
| Ethylene glycol | | 2.5 | 10:0 | 8:1 |
| Furadan + ethylene glycol | 25 + | 2.5 | 34:0.3 | 15:1 |
| 1,2-propanediol | | 2.5 | 4:0.3 | 0:1 |
| Furadan + 1,2-propanediol | 25 + | 2.5 | 24:0.3 | 24:1 |
| 1,4-butanediol | | 2.5 | 0:1 | 16:2 |
| Furadan + 1,4-butanediol | 25 + | 2.5 | 57:1 | 52:2 |
| 1,3-butanediol | | 2.5 | 6:0.3 | 4:1 |
| Furadan + 1,3-butanediol | 25 + | 2.5 | 31:0 | 22:1 |
| Tween 20 Control | | 0.05 | 0:0 | 0:0 |
| Untreated Controls | | | 0:0 | 0:0 |

From the data of Table II the effectiveness of the diols in enhancing the miticidal activity of the compositon is evidenced by comparison with the effectiveness of the miticide without diol, i.e. 4%; 2% mortality (For this determination, the miticide is formulated by dissolution in acetone followed by dilution with de-ionized water containing 0.05% Tween 20).

EXAMPLE 3

The contact miticidal effectiveness of 1,3-butanediol, alone, is determined using the procedure of Example I with the results being tabulated in Table III.

TABLE III

| Percent Conc. (in water-0.05% Tween 20) | % Mortality (3 days) | Plant injury |
|---|---|---|
| 25 | 75 | 9.3 |
| 20 | 86 | 9 |
| 15 | 52 | 6.3 |
| 10 | 38 | 4.3 |
| 5 | 11 | 4 |
| 2 | 3 | 1 |
| 1 | 2 | 1 |

EXAMPLE 4

1-Naphthyl N-methyl carbamate (Sevin) is dissolved at varying concentrations in 1,3-butanediol which is then diluted with a housefly spray base consisting of cyclohexanone and refined kerosene to obtain formulations containing 2500, 5000 and 10,000 ppm Sevin in 50%, 25% and 10% diol. The preparations containing 25% and 50% diol are not stable and tend to separate almost immediately on standing.

These formulations are tested against houseflies (M. domestica, adults) by spray application with the results being tabulated in Table IV, the results being for three separate determinations with the average thereof indicated for each formulation.

TABLE IV

| Material Applied | Conc(ppm) Sevin | % 1-Hour Knockdown:24-Hour Mortality | | | |
|---|---|---|---|---|---|
| | | A | B | C | Average |
| Sevin | 2,500 | 13:8 | 11:2 | 85:60 | 36:23 |
| | 5,000 | 64:42 | 93:81 | 84:60 | 80:61 |
| | 10,000 | 85:61 | 81:59 | 87:83 | 84:67 |
| 1,3-butanediol (50%) + Sevin | 2,500 | 28:18 | 13:24 | 29:29 | 23:23 |
| | 5,000 | 5:11 | 87:70 | 21:27 | 37:36 |
| | 10,000 | 48:36 | 64:60 | 67:60 | 59:65 |
| 1,3-butanediol (25%) + Sevin | 2,500 | 5:1 | 50:42 | 50:31 | 35:26 |
| | 5,000 | 90:84 | 70:67 | 86:70 | 82:73 |
| | 10.000 | 87:48 | 87:75 | 100:88 | 91:70 |
| 1,3-butanediol (10%) + Sevin | 2,500 | 67:51 | 78:78 | 69:49 | 71:59 |
| | 5,000 | 87:82 | 92:82 | 100:94 | 93:86 |
| | 10,000 | 100:93 | 100:100 | 97:89 | 99:94 |
| 50% BG | | 3:6 | 8:8 | 8:14 | 6:9 |
| 25% BG | | 13:10 | 4:4 | 6:6 | 7:7 |
| 10% BG | | 4:4 | 21:39 | 11:11 | 12:18 |
| Untreated Controls | | 0:0 | 0:0 | 0:0 | 0:0 |

EXAMPLE 5

Aqueous formulations of m-[N-(dimethyl-aminomethylene)amino] phenyl N-methyl carbamate (Carzol) at various levels containing 5% 1,3-butanediol are tested against Southern Army worm eggs by contact spray application. The results are tabulated in Table V for concentration levels of Carzol at 25, 50 and 100 ppm.

TABLE V

Potentiation of Ovicidal Activity of Carzol against Southern Armyworm Eggs

| Con. Carzol | Con. 1,3-butanediol % | % Mortality |
|---|---|---|
| 100 | 0 | 26 |
| 100 | 5 | 56 |
| 50 | 0 | 27 |
| 50 | 5 | 62 |
| 25 | 0 | 21 |
| 25 | 5 | 53 |

The test procedure employed for these data is as follows. Individually potted horticultural bean plants in first true leaf growth stage are used as host plants. Five third in-star larvae are caged in each plant with three plants in each unit. Upper and lower surfaces of foliar portions are alternatively sprayed at 20 psi to incipient run off, allowed to air dry under laboratory conditions and then are removed to greenhouse holding racks provided with subterranean water source. At the end of 72 hours, observations are made for insect mortality.

EXAMPLE 6

Furadan is tested as a stomach poison against Southern Army Larvae (*Spodoptera eridania*) with and without 1,3-butanediol at various levels (25, 50 and 100 ppm) of Furadan at different levels of the diol (1%, 2.5% and 5.0%) but no significant potentiation of Furadan is noted at the 25 or 50 ppm level for any level of the diol. At 100 ppm Furadan, 100% control is obtained without the diol being present.

Similarly, Furadan on testing as a stomach poison for Mexican Bean Beetle Larvae (*Epilachna varivestis*) showed no significant enhancement by 1,3-butanediol.

In these tests, individually potted horticultural bean plants in first true leaf growth stage are used as host plants. Upper and lower surfaces of foliar portions are alternately sprayed at 20 psi to incipient run off, allowed to air dry under laboratory conditions and then are removed to greenhouse holding racks provided with subterreanean water source. Fine third-instar larvae are caged on each plant for 72 hours, with three such plants being used for each unit.

At the end of the 72 hour holding period, observations are made for insect mortality.

What is claimed is:

1. An insecticidal composition comprising 1-naphthyl N-methyl carbamate and an alkanediol of up to about 6 carbon atoms in an amount sufficient to enhance the activity of said carbamate, said carbamate being present in an amount from about 0.05 to about 10% by weight of the alkanediol.

2. A composition according to claim 1 wherein the alkanediol is a butanediol.

3. An insecticidal composition comprising (2,3-dihydro-2, 2-dimethyl-7-benzofuranyl) N-methyl carbamate and an alkanediol of up to about 6 carbon atoms in an amount sufficient to enhance the activity of said carbamate, said carbamate being present in an amount from about 0.05 to about 10% by weight of the alkanediol.

4. A composition according to claim 3 wherein the alkanediol is a butanediol.

5. An insecticidal composition comprising m-[N-(dimethylaminomethylene) amino] phenyl N-methyl carbamate and an alkanediol of up to about 6 carbon atoms in an amount sufficient to enhance the activity of said carbamate, said carbamate being present in an amount from about 0.05 to about 10% by weight of the alkanediol.

6. A composition according to claim 5 wherein the alkanediol is a butanediol.

* * * * *